United States Patent [19]

Akers et al.

[11] 4,427,572

[45] Jan. 24, 1984

[54] PROCESS FOR THE MANUFACTURE OF SOAP

[75] Inventors: John B. Akers, South Wirral; Jane A. Littler, Warrington; David C. Peters, Heswall, all of England

[73] Assignee: Lever Brothers Company, New York, N.Y.

[21] Appl. No.: 285,665

[22] Filed: Jul. 21, 1981

[30] Foreign Application Priority Data

Jul. 24, 1980 [GB] United Kingdom ................ 8024344

[51] Int. Cl.$^3$ .............................................. C11D 13/00
[52] U.S. Cl. ..................................................... 252/369
[58] Field of Search ............................................ 252/369

[56] References Cited

U.S. PATENT DOCUMENTS

| | | | |
|---|---|---|---|
| 2,332,202 | 10/1943 | Culkins | 252/369 |
| 2,380,650 | 7/1945 | Jacobs | 252/369 |
| 2,383,630 | 8/1945 | Trent | 252/369 |
| 3,376,327 | 4/1968 | Freeland | 252/369 |
| 4,075,234 | 2/1978 | Peterson | 260/417 |

OTHER PUBLICATIONS

Seifen-Ole-Fette-Wachse, 102 459 (1976).
Kirk-Othmer "Encyclopedia of Chemical Technology", vol. 14, (1967) pp. 835–837.
"Handbook of Chemistry and Physics", 57th Ed., (1976–1977), pp. E55–E58.

*Primary Examiner*—Norman Morgenstern
*Assistant Examiner*—Janyce A. Bell
*Attorney, Agent, or Firm*—Milton L. Honig; James J. Farrell

[57] ABSTRACT

A calcium soap is prepared by saponifying an organic carboxylic acid having from 6 to 24 carbon atoms in the molecule, its ester or mixtures thereof with calcium hydroxide in a liquid reaction medium comprising a dipolar aprotic solvent, separating the calcium soap from the reaction medium and removing excess of the solvent from the calcium soap. The calcium soap so produced is in the form of a dry finely divided powder which can, for example, be employed in the manufacture of industrial lubricants.

5 Claims, No Drawings

PROCESS FOR THE MANUFACTURE OF SOAP

The invention relates to a process for the production of soap by saponifying organic acid esters or free fatty acids. More particularly, the invention relates to a process for the production of calcium soaps from oils, fats or free fatty acids.

The production of calcium soaps is usually carried out by heating an oil or fat, comprising organic acid esters, with calcium hydroxide (lime) under substantially anhydrous conditions. The reaction generally involves the consumption of a considerable amount of heat energy and usually takes several days to complete.

We have now discovered that calcium soaps can be produced by the saponification of oils, fats or free fatty acids with powdered calcium hydroxide in the presence of a dipolar aprotic solvent, at a lower temperature than is conventionally employed, and in a shorter time than is generally the experience in the production of calcium soaps on an industrial scale.

It should be explained that the expressions "saponification" and "saponifying" are normally employed in describing the process of reacting an oil or fat with an alkali metal or alkaline earth metal hydroxide to form the corresponding metallic soap. In the present specification, however, as will be made clear, soap can also be prepared by reacting a free fatty acid with an alkali metal or alkaline earth metal hydroxide: this latter reaction is accordingly also described herein by the expressions "saponification" and "saponifying".

Accordingly, the invention provides a process for the production of calcium soap, which comprises saponifying an organic carboxylic acid, its esters or mixtures thereof with calcium hydroxide in a liquid reaction medium comprising a dipolar aprotic solvent, separating the calcium soap from the reaction medium and removing excess dipolar aprotic solvent from the calcium soap.

The organic carboxylic acid that can be used as starting material for the saponification process can be an alkyl or aryl acid having from 6 to 24 carbon atoms in its molecule, or mixtures of such acids. A convenient source of organic carboxylic acid is a commercial grade source of free fatty acids derived for example from the processing of crude fats, oils and other lipids of animal or vegetable origin.

The organic carboxylic acid esters that can be used as starting material for the saponification process can be simple alkyl or aryl esters having from 6 to 24 carbon atoms in the molecule, or they can be glyceride esters such as triglycerides which typically constitute the major proportion of the materials present in fats and oils derived from animal or vegetable sources, as well as mono and di-glycerides or mixtures thereof with triglycerides. Specific non-limiting examples of animal or vegetable fats and oils include lard, tallow, coconut oil, palm oil, various by-products from animal rendering operations, oil from oleaginous seeds such as soybean, sunflower seed and cottonseed.

The liquid medium in which the saponification reaction is conducted comprises a bipolar aprotic solvent in an amount at least sufficient to dissolve the organic acid or its ester.

The dipolar aprotic solvent is one which, according to Parker in Chemical Reviews, 69, No 1, February 1969 at page 2, has a dielectric constant above 15. The preferred dipolar aprotic solvent is acetone which has a dielectic constant of 20.7.

The liquid medium will also normally comprise at least a minor amount of water derived from that present in the ingredients of the reaction medium. It is however important to ensure that the amount of water present in the reaction mixture is not excessive such that the soap formed as a result of saponification does not lose its grainy, powdery character and become sticky and intractable due to excessive hydration.

The amount of calcium hydroxide to be employed will generally depend on whether the starting material to be saponified comprises free organic acid, organic acid ester or mixtures thereof, on the amount of the starting material and on the Saponification Value of the starting material.

The Saponification Value is defined as the number of milligrams of potassium hydroxide required for complete saponification of one gram of free organic acid and/or organic acid ester. The Saponification Value can be determined by the method described in "The Industrial Chemistry of the Fats and Waxes", by Hilditch (1949) at page 42.

The amount of calcium hydroxide employed in order to completely saponify the free organic acid and/or organic acid ester can accordingly be calculated from the Saponification Value of the starting material and will, in theory, be the stoichiometric amount. In practice, however, it is preferred to employ slightly less than the stoichiometric amount of calcium hydroxide in order to ensure that the soap that is formed is not contaminated with unused calcium hydroxide. Ideally the amount of calcium hydroxide employed can be considerably less than the stoichiometric amount, for example, as little as 50% of the stoichiometric amount, any unsaponified organic acid or ester remaining in solution in the acetone being separated and recovered and, if desired, added to further starting material for subsequent saponification. It is to be understood, however, that an amount of calcium hydroxide in excess of the stoichiometric amount, for example, up to 10% more than the stoichiometric amount, can be employed if complete saponification of the organic acid or ester is to be achieved.

In carrying out the process of the invention for the preparation of a calcium soap, the organic carboxylic acid or its ester or mixtures thereof are saponified with cslcium hydroxide in a liquid reaction medium comprising a dipolar aprotic solvent. The calcium soap so formed is separated from the reaction medium and excess solvent is removed from the soap or soaps.

In a preferred process, the organic acid or ester thereof is first dissolved in acetone and the calcium hydroxide in a dry state is then added with stirring. The liquid reaction mixture can be heated to a temperature of about 56° C., this being the boiling point of acetone, without application of superatmospheric pressure, and saponification allowed to proceed, preferably under reflux until complete.

Soap is formed as a solid finely divided powder in the reaction vessel and this can then be removed readily, for example by filtration and then desolventised to remove acetone, for example by the application of steam, to yield dry finely divided soap powder.

The duration of the saponification process will generally depend on the temperature of the process and on the Acid Value of the organic acid ester, if any, which is saponified. The saponificaton reaction is generally exothermic and is preferably initiated by gentle heating to enable the reaction to proceed at about the boiling point of the dipolar aprotic solvent (56° C. for acetone) at normal atmospheric pressure. The process can alternatively be carried out at higher temperatures, provided that a pressure in excess of that of normal atmospheric pressure is applied.

The Acid Value is defined as the number of milligrams of potassium hydroxide required exactly to neutralise the free acidity in one gram of the organic acid ester. The Acid Value can be determined by the method described in "The Industrial Chemistry of the Fats and Waxes" by Hilditch (1949) at page 43.

The calcium soap obtained as a result of saponification will be precipitated as a fine powder, generally having a particle size ranging from 0.05 mm to 1 mm. In one example to be illustrated in greater detail later in this specification, the average particle size was between 0.2 to 0.3 mm.

The soap powder will generally have a moisture content of from 2 to 10% by weight of water. Accordingly, if it is desired to obtain soap powder with a higher moisture content, it is preferred to desolventise the soap powder by steaming it after filtration or otherwise separating it from the liquid reaction medium, so as to drive off any residual dipolar aprotic solvent, and at the same time to adjust the moisture in the soap to the desired level.

The soap powder produced by this method will generally be creamy-white in colour and substantially free from much of the coloured matter, including unsaponifiable matter commonly present in commercial or crude grades of animal fats and oils or oily distillates, which can be used as inexpensive sources of organic acids or organic acid esters, the coloured matter ramaining in solution in the dipolar aprotic solvent medium.

Typically, yields of soap obtained by the process of the invention can be as high as 90% or higher.

The calcium soaps prepared according to the invention as a finely divided powder can be used in the manufacture of industrial lubricants for use for example in wire drawing.

The invention is illustrated by the following Examples:

EXAMPLE 1

This Example illustrates the production of calcium soaps from solvent extracted sewage grease, which forms a source of free organic acids and organic acid esters.

100 g of sewage grease containing 5 g hexane was dissolved in 100 ml acetone as the dipolar aprotic solvent and heated with stirring at a temperature of 56° C. The weight ratio of acetone to grease was accordingly 0.8:1.

12 g of powdered anhydrous calcium hydroxide was then added and saponification was allowed to proceed for 3 hours.

The soap powder so formed had a fine grain appearance. Three acetone washings with a total of 250 ml of acetone at 56° C. for 30 minutes were made.

90% of the saponifiable material in the grease was converted to calcium soaps, 18% of ester materials being saponified. The final level of unsaponifiables was 4.3% of the total fatty matter, 83% of the total fatty matter being recoverable as soap.

EXAMPLE 2

This Example illustrates the production of calcium soaps from PRIFAC 7920, a source of free fatty acids obtained as a main distillation fraction from split tallow fatty acids. 100 g of PRIFAC 7920 was dissolved in 100 g acetone at 56° C.

15 g powdered anhydrous calcium hydroxide was then added: this represented an excess of 10% of the theoretical stoichiometric amount. Saponification was allowed to proceed at 56° for 15 minutes.

The soap powder so formed had a fine grain appearance.

The yield of calcium soaps from this starting material was 100%.

The fatty acid analysis of PRIFAC 7920 is as follows:

| Fatty Acid | % w/w |
|---|---|
| $C_{14}$ | 2 |
| $C_{16}$ | 25 |
| $C_{16:1}$ | 3 |
| $C_{18}$ | 18 |
| $C_{18:1}$ | 44 |
| $C_{18:2}$ | 6 |
| $C_{18:3}$ | 1 |
| $C_{20}$ | 1 |
| Saponification Value | 201–207 |
| Acid Value | 200–206 |
| Iodine Value | 50–60 |

What is claimed is:
1. A process for the production of calcium soap, which comprises saponifying an organic carboxylic acid having from 6 to 24 carbon atoms in the molecule, its ester or mixtures thereof with calcium hydroxide in a liquid reaction medium comprising a dipolar aprotic solvent having a dielectric constant of above 15, separating the calcium soap from the reaction medium, and removing excess dipolar aprotic solvent from the calcium soap.

2. The process according to claim 1, wherein the organic carboxylic acid is an alkyl or aryl acid having from 6 to 24 carbon atoms in the molecule, or a mixture of such acids.

3. The process according to claim 1, wherein the organic carboxylic acid ester is an alkyl or aryl ester having from 6 to 24 carbon atoms in the molecule.

4. The process for the production of calcium soap, which comprises saponifying an organic carboxylic acid having from 6 to 24 carbon atoms in the molecule, its ester or mixtures thereof with calcium hydroxide in a liquid reaction medium comprising acetone, separating the calcium soap from the reaction medium, and removing excess acetone from the calcium soap.

5. A process for the preparation of calcium soaps which comprises the steps of:
 (i) saponifying lipid material selected from the group consisting of free fatty acids, fats, oils and mixtures thereof with an amount of solid calcium hydroxide which is from 50% less to 10% more than the stoichiometric amount, in a liquid reaction medium comprising acetone;
 (ii) separating the calcium soaps from the reaction mixture; and
 (iii) removing excess acetone from the calcium soaps.

* * * * *